US012781181B2

(12) United States Patent
Liu et al.

(10) Patent No.: US 12,781,181 B2
(45) Date of Patent: Nov. 3, 2026

(54) **AMMONIUM SULFATE-TOLERANT *SACCHAROMYCES CEREVISIAE* AND SCREENING METHOD THEREOF**

(71) Applicant: INNER MONGOLIA UNIVERSITY OF TECHNOLOGY, Hohhot (CN)

(72) Inventors: Zhanying Liu, Hohhot (CN); Le Zhang, Hohhot (CN); Xiaoming Su, Hohhot (CN)

(73) Assignee: INNER MONGOLIA UNIVERSITY OF TECHNOLOGY, Hohhot (CN)

( * ) Notice: Subject to any disclaimer, the term of this patent is extended or adjusted under 35 U.S.C. 154(b) by 335 days.

(21) Appl. No.: 18/534,890

(22) Filed: Dec. 11, 2023

(65) Prior Publication Data

US 2024/0409882 A1 Dec. 12, 2024

Related U.S. Application Data

(63) Continuation of application No. PCT/CN2023/125908, filed on Oct. 23, 2023.

(30) Foreign Application Priority Data

Jun. 9, 2023 (CN) ......................... 202310678280.0

(51) Int. Cl.
*C12N 1/185* (2026.01)
*C12Q 1/02* (2006.01)
*C12R 1/865* (2006.01)

(52) U.S. Cl.
CPC ............... *C12N 1/185* (2021.05); *C12Q 1/02* (2013.01); *C12R 2001/865* (2021.05)

(58) Field of Classification Search
CPC .. C12N 1/185; C12N 1/18; C12Q 1/02; C12R 2001/865
See application file for complete search history.

(56) References Cited

PUBLICATIONS

Mendes-Ferreira A, Mendes-Faia A, Leão C. Growth and fermentation patterns of *Saccharomyces cerevisiae* under different ammonium concentrations and its implications in winemaking industry. J Appl Microbiol. 2004;97(3):540-5. doi: 10.1111/j.1365-2672.2004.02331.x. PMID: 15281934. (Year: 2004).*

* cited by examiner

*Primary Examiner* — Kade Ariani
(74) *Attorney, Agent, or Firm* — HOWARD M COHN and Associates, LLC

(57) ABSTRACT

The present invention discloses a strain of ammonium sulfate-tolerant *Saccharomyces cerevisiae*, and a screening method thereof. The strain of ammonium sulfate-tolerant *Saccharomyces cerevisiae*, named *Saccharomyces cerevisiae* Z-1, was preserved in Guangdong Microbial Culture Collection Center on Mar. 3, 2023, with a preservation number of GDMCC NO: 63227 and a preservation address of Floor 5, Building 59, No. 100 Courtyard, Xianlie Middle Road, Guangzhou. The ammonium sulfate-tolerant *Saccharomyces cerevisiae* Z-1 provided by the present invention may grow and breed in an environment containing 1.0 mol/L $NH_4^+$ (6.6% ammonium sulfate), and the protein content of the strain can reach 51.97%; and as a fermentation strain for protein feed, the strain of the present invention not only can adapt to the high-tolerance environment, but also can increase the protein content of the protein feed, and is an excellent strain for solid-state fermentation.

7 Claims, 7 Drawing Sheets

AMMONIUM SULFATE-TOLERANT *SACCHAROMYCES CEREVISIAE* AND SCREENING METHOD THEREOF

TECHNICAL FIELD

The present invention relates to the technical field of biology, and particularly relates to an ammonium sulfate-tolerant *Saccharomyces cerevisiae* and a screening method thereof.

BACKGROUND

*Saccharomyces cerevisiae* has lots of advantages of short growth period, strong fermentation capacity, easy large-scale culture and rich nutrients such as various proteins, amino acids, vitamins, bioactive substances, etc., and is widely used in food, medicine, and other fields. At the same time, *Saccharomyces cerevisiae* is also usually regarded as a main fermentation strain of protein feed. Adding *Saccharomyces cerevisiae* into the protein feed may effectively increase the nutritive value of the feed and improve the growth and development of animals, and may also improve the taste and palatability of the feed and increase the fragrance of the feed, thereby improving the appetite and food intake of the animals for the feed. In addition, *Saccharomyces cerevisiae* is also rich in organic acids and antibiotics, which may replace some antibiotics, thereby reducing the breeding cost. The protein content and tolerance of *Saccharomyces cerevisiae* in the fermentation process are always a research focus at present. In the production of protein feed, ammonium sulfate provides a nitrogen source for the growth of strains, but high-concentration ammonium sulfate may inhibit the growth of *Saccharomyces*. The use of salt-tolerant *Saccharomyces cerevisiae* for fermenting the protein feed can enhance the stress resistance, so that the protein feed grows and ferments normally in a hyperosmotic environment, thereby improving the stability and quality of products.

SUMMARY

The present invention aims at overcoming the disadvantages of the prior art, and providing a strain of ammonium sulfate-tolerant *Saccharomyces cerevisiae* and a screening method thereof. The ammonium sulfate-tolerant *Saccharomyces cerevisiae* can grow and breed in an environment with relatively high concentration of ammonium sulfate, and is an excellent strain for solid-state fermentation of protein feed.

To realize the above purpose, the present invention adopts the following technical solutions:

A strain of ammonium sulfate-tolerant *Saccharomyces cerevisiae*, named *Saccharomyces cerevisiae* Z-1, was preserved in Guangdong Microbial Culture Collection Center on Mar. 3, 2023, with a preservation number of GDMCC NO: 63227 and a preservation address of Floor 5, Building 59, No. 100 Courtyard, Xianlie Middle Road, Guangzhou.

Further, the *Saccharomyces cerevisiae* Z-1 can grow and breed in an environment containing 1.0 mol/L $NH_4^+$.

The present invention further provides a screening method of the ammonium sulfate-tolerant *Saccharomyces cerevisiae*, which includes the following steps:

S1: separating a plurality of strains of *Saccharomyces cerevisiae* from natural fermentation broth of grapes, obtaining seed solutions, and numbering the seed solutions of the plurality of strains of *Saccharomyces cerevisiae*;

S2: preliminarily screening salt-tolerant *Saccharomyces cerevisiae*: inoculating the seed solutions of *Saccharomyces cerevisiae* numbered in S1 to ammonium sulfate agar culture media with different concentrations of $NH_4^+$ respectively for culture, and screening 3-5 strains of *Saccharomyces cerevisiae* with large and full bacterial colonies;

S3: determining growth curves: inoculating the seed solutions of *Saccharomyces cerevisiae* numbered in S1 into YPD liquid culture medium respectively for culture, drawing growth curves, determining a stable growth period, and screening 3-5 strains of *Saccharomyces cerevisiae* with excellent growth during the stable growth period;

S4: determining protein content: inoculating the seed solutions of *Saccharomyces cerevisiae* numbered in S1 into the YPD liquid culture medium for culture to obtain bacterial suspensions, measuring the protein content in the bacterial suspensions after the culture, and screening 3-5 strains of *Saccharomyces cerevisiae* with high protein content;

S5: comprehensively analyzing and comparing *Saccharomyces cerevisiae* screened in S2, S3 and S4 to select the high-protein strain of *Saccharomyces cerevisiae* with high salt tolerance and excellent growth.

Further, 15 strains of *Saccharomyces cerevisiae* are separated from the natural fermentation broth of grapes in step S1 and numbered respectively as: Z-1, Z-2, Z-3, Z-4, Z-5, Z-6, 1-1, 1-2, 1-3, 1-4, 1-5, 1-6, 1-7, 1-8 and 1-9.

Further, specific operation steps of determining the growth curves in step S2 are as follows: collecting 4 μL of the seed solutions of the 15 separated strains of *Saccharomyces cerevisiae*, orderly spotting the seed solutions on ammonium sulfate agar culture media containing 0 mol/L, 0.2 mol/L, 0.4 mol/L, 0.6 mol/L, 0.8 mol/L, 1.0 mol/L, and 1.2 mol/L $NH_4^+$, and invertedly culturing for 48 h at 30° C. in a thermostatic incubator; and repeating 3 times for each level, and screening *Saccharomyces cerevisiae* with large and full bacterial colonies after 48 h culture.

Further, a specific method of determining the growth curves in step S3 is as follows: inoculating the seed solutions of the 15 strains of *Saccharomyces cerevisiae* separated in step S1 respectively into 300 mL YPD liquid culture medium at an inoculation amount of 1%, preparing a group of blank control without inoculating the seed solution of *Saccharomyces cerevisiae* at the same time, conducting shaking culturing at 30° C. and 180 rpm, collecting 3 mL of sample respectively at 0 h, 2 h, 4 h, 6 h, 8 h, 10 h, 12 h, 14 h, 16 h, 18 h, 20 h, 22 h and 24 h after inoculation, setting zero for the blank control, determining a light absorption value of *Saccharomyces cerevisiae* at 600 nm, then drawing the growth curve with the light absorption value of *Saccharomyces cerevisiae* as a vertical axis and growth time as a horizontal axis, and screening 3-5 strains of *Saccharomyces cerevisiae* with excellent growth during the stable growth period.

Further, a specific method of determining the protein content in step S4 is as follows: inoculating the seed solutions of the 15 strains of *Saccharomyces cerevisiae* separated in the step S1 respectively into 300 mL YPD liquid culture medium at the inoculation amount of 1%, and conducting shaking culturing for 48 h at 30° C. and 180 rpm to obtain the bacterial suspensions; determining the protein content in each bottle of bacterial suspension; and screening 3-5 strains of *Saccharomyces cerevisiae* with high protein content.

Further, $OD_{600}$ of the seed solutions of *Saccharomyces cerevisiae* in the steps S2, S3 and S4 is the same.

Further, when the protein content in each bottle of bacterial suspension is determined in the step S4, each group is repeated three times, and a specific operation method is as follows:

centrifuging the bacterial suspension at 4500 rpm for 10 min after 48 h fermentation culture, removing supernatant, washing with distilled water, repeatedly washing three times, drying to constant weight in an oven at 105° C. or freeze drying to constant weight, cooling, and then determining the crude protein content by a protein content determination method specified in GB/T 5009.5-2003 as follows:

$$\text{crude protein (\%)} = \frac{(V_2 - V_1) \times C \times 0.0140 \times 6.25}{m \times V'/V} \times 100$$

In the formula, $V_2$—volume mL of standard hydrochloric acid solution consumed by titration of samples;

$V_1$—volume mL of the standard hydrochloric acid solution required for the blank control;

C—concentration of the standard hydrochloric acid solution;

m—mass g of a test sample;

V—total volume mL of a test sample digestion solution;

V'—volume mL of the digestion solution for distillation;

0.0140—grams of nitrogen per milligram equivalent;

6.25—an average coefficient for converting nitrogen into proteins.

Compared with the prior art, the present invention has the following beneficial effects:

The ammonium sulfate-tolerant *Saccharomyces cerevisiae* Z-1 provided by the present invention may grow and breed in an environment containing 1.0 mol/L $NH_4^+$ (6.6% ammonium sulfate (W/V)), and not only can adapt to a hyperosmotic environment of solid-state fermentation, but also can be transformed into proteins by using the relatively cheap ammonium sulfate inorganic salt. Compared with the existing bacterial strains, the protein content of the strain of the present invention can reach 51.97%; and as the fermentation strain for the protein feed, the strain of the present invention not only can adapt to the high tolerance environment, but also can increase the protein content of the protein feed, and is an excellent strain for solid-state fermentation.

DETAILED DESCRIPTION

The present invention is further described below in combination with drawings and embodiments, and the present invention includes but is not limited to the following embodiments.

The present embodiment provides a strain of ammonium sulfate-tolerant *Saccharomyces cerevisiae*, named *Saccharomyces cerevisiae* Z-1 and preserved in Guangdong Microbial Culture Collection Center (GDMCC) on Mar. 3, 2023, with a preservation number of GDMCC NO: 63227 and a preservation address of Floor 5, Building 59, No. 100 Courtyard, Xianlie Middle Road, Guangzhou.

The embodiment further provides a screening method of the ammonium sulfate-tolerant *Saccharomyces cerevisiae*; and the ammonium sulfate-tolerant *Saccharomyces cerevisiae* is separated from natural fermentation broth of grapes and screened by the following steps:

(1) Separating 15 strains of *Saccharomyces cerevisiae* from the natural fermentation broth of grapes, obtaining seed solutions, and numbering the seed solutions of the 15 strains of *Saccharomyces cerevisiae* as Z-1, Z-2, Z-3, Z-4, Z-5, Z-6, 1-1, 1-2, 1-3, 1-4, 1-5, 1-6, 1-7, 1-8 and 1-9.

Figure 1:
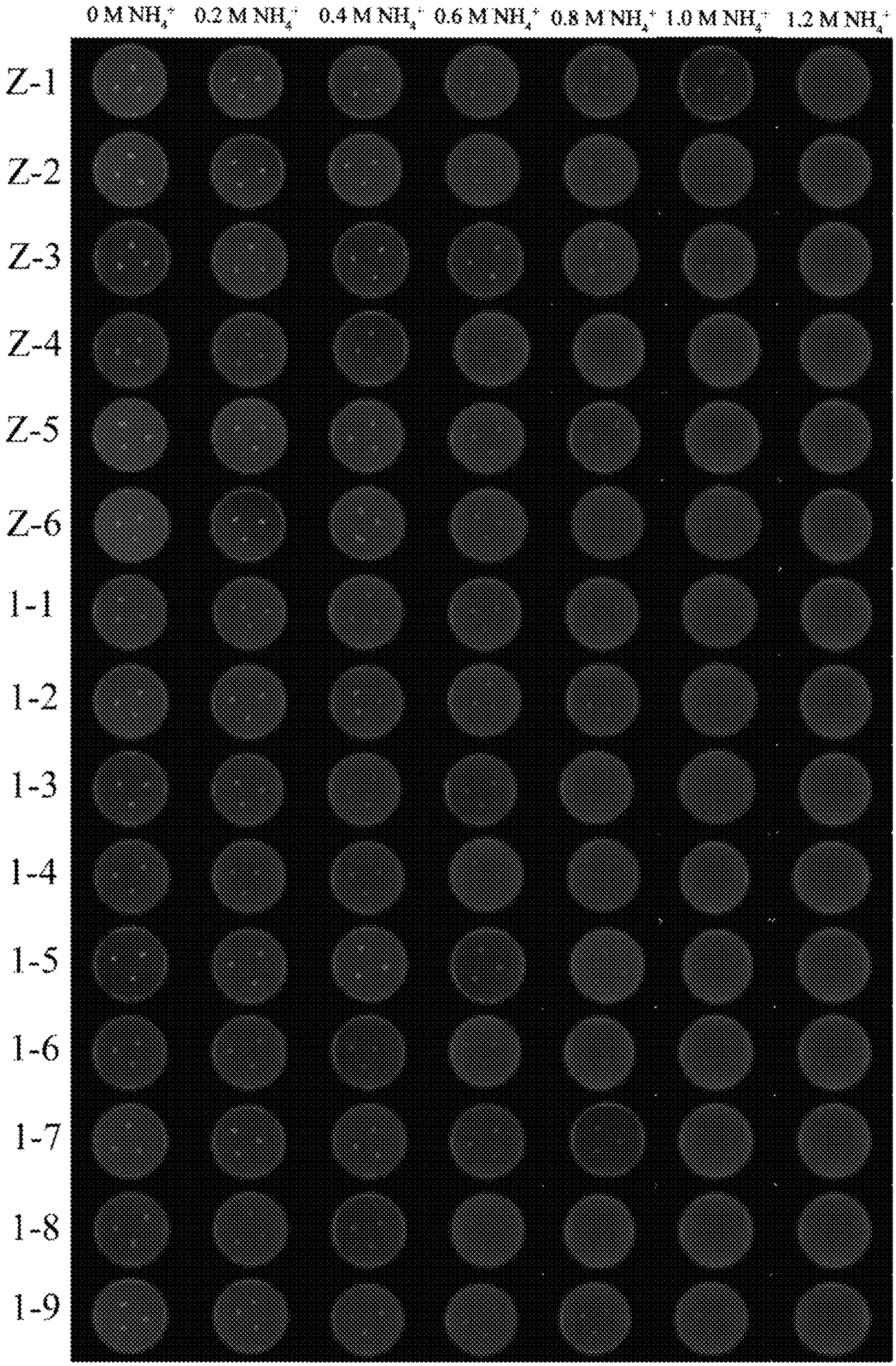
FIG. 1 shows growth situation of salt-tolerant *Saccharomyces cerevisiae* preliminarily screened in the present invention.

(2) Preliminarily Screening Salt-Tolerant *Saccharomyces cerevisiae:* collecting 4 μL of the seed solutions of the 15 strains of *Saccharomyces cerevisiae* separated in (1), orderly spotting the seed solutions on ammonium sulfate agar culture medium containing 0 mol/L, 0.2 mol/L, 0.4 mol/L, 0.6 mol/L, 0.8 mol/L, 1.0 mol/L, and 1.2 mol/L $NH_4^+$, and invertedly culturing for 48 h at 30° C. in a thermostatic incubator; repeating 3 times for each level (inoculating the seed solution three times into each culture medium, and obtaining three bacterial colonies, as shown in FIG. 1), and screening *Saccharomyces cerevisiae* with large and full bacterial colonies after 48 h culture.

After 48 h culture, observing the above 15 strains of *Saccharomyces cerevisiae*, with growth situation shown in FIG. 1. It may be seen from the drawing that all strains can grow in the presence of 0-0.6 mol/L $NH_4^+$, there is no obvious difference in the growth of all strains, and the colony size decreases with the increase of the salt concentration. *Saccharomyces cerevisiae* Z-1, Z-2, Z-3, Z-5, 1-1, 1-2, 1-3, 1-5, 1-7 and 1-9 can grow in the presence of 0.8 mol/L $NH_4^+$, but most colonies are small in diameter and not dense; and only the colonies of *Saccharomyces cerevisiae* Z-1 and *Saccharomyces cerevisiae* Z-3 are larger and fuller. In the presence of 1.0 mol/L $NH_4^+$, only *Saccharomyces cerevisiae* Z-1 and *Saccharomyces cerevisiae* Z-3 can grow, the colony of *Saccharomyces cerevisiae* Z-3 is smaller, and the colony of *Saccharomyces cerevisiae* Z-1 is larger. In the presence of 1.2 mol/L $NH_4^+$, all strains do not grow. It indicates that *Saccharomyces cerevisiae* Z-1 and *Saccharomyces cerevisiae* Z-3 have strong salt tolerance, and the salt tolerance of *Saccharomyces cerevisiae* Z-1 is stronger than that of *Saccharomyces cerevisiae* Z-3.

(3) Determining Growth Curves:

Inoculating the seed solutions of the 15 strains of *Saccharomyces cerevisiae* separated in (1) respectively into 300 mL YPD liquid culture medium at an inoculation amount of 1% ($OD_{600}$=0.8), and preparing a group of blank control without inoculating the seed solution of *Saccharomyces cerevisiae* at the same time. Conducting shaking culturing at 30° C. and 180 rpm, collecting 3 mL of sample respectively at 0 h, 2 h, 4 h, 6 h, 8 h, 10 h, 12 h, 14 h, 16 h, 18 h, 20 h, 22 h and 24 h after inoculation, setting zero for the blank control, determining a light absorption value of *Saccharomyces cerevisiae* at 600 nm, then drawing the growth curve with the light absorption value of *Saccharomyces cerevisiae* as a vertical axis and growth time as a horizontal axis, and selecting the best strain according to the growth situation in the stable growth period.

Figure 2:
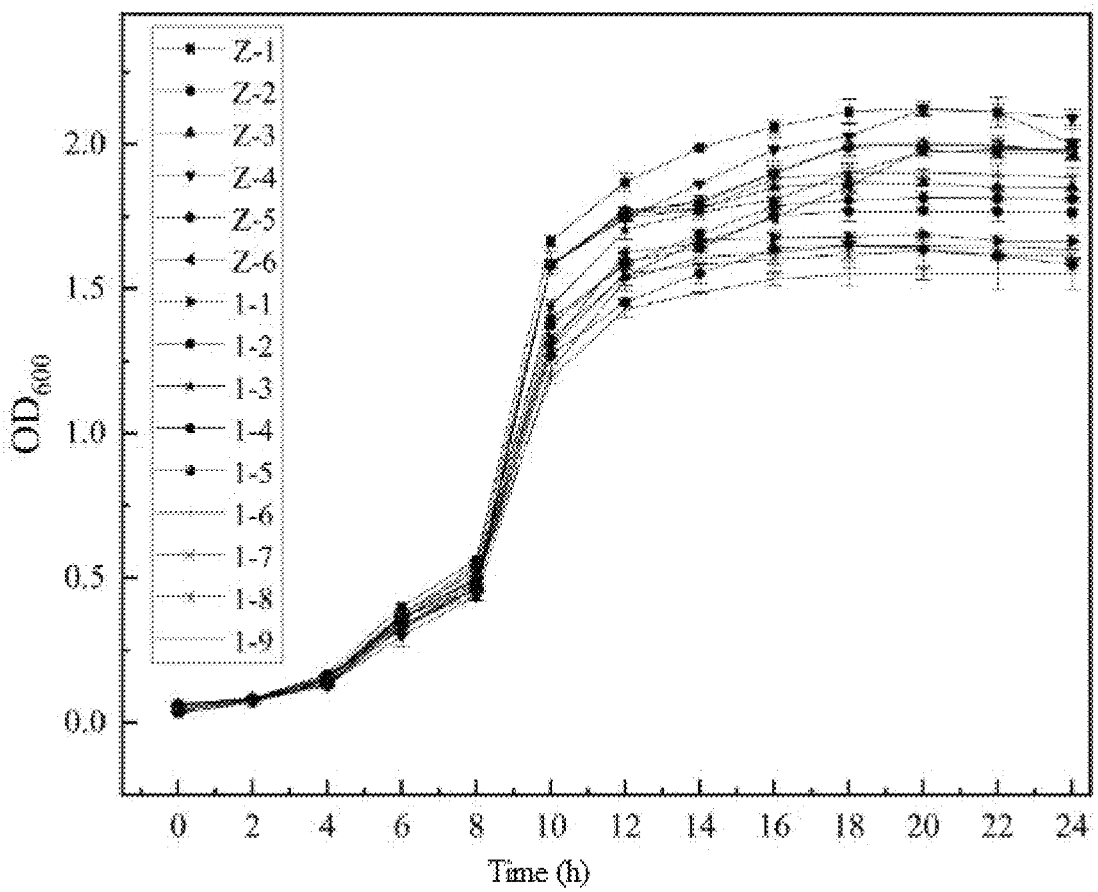
FIG. 2 is a diagram of growth curve determination results in the present invention.
Figure 3:
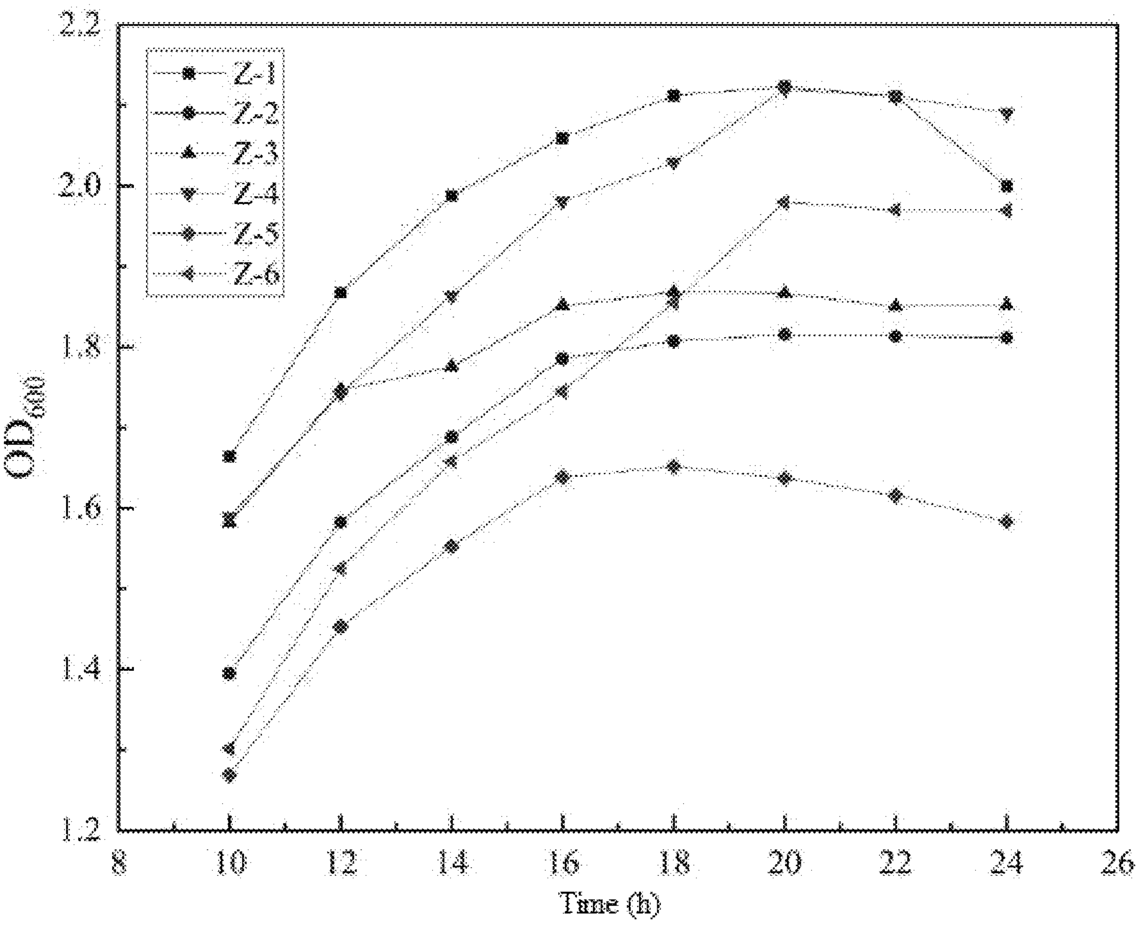
FIG. 3 is a growth curve chart of *Saccharomyces cerevisiae* Z-1, Z-2, Z-3, Z-4, Z-5 and Z-6 in a stable growth period (14-20 h)
Figure 4:
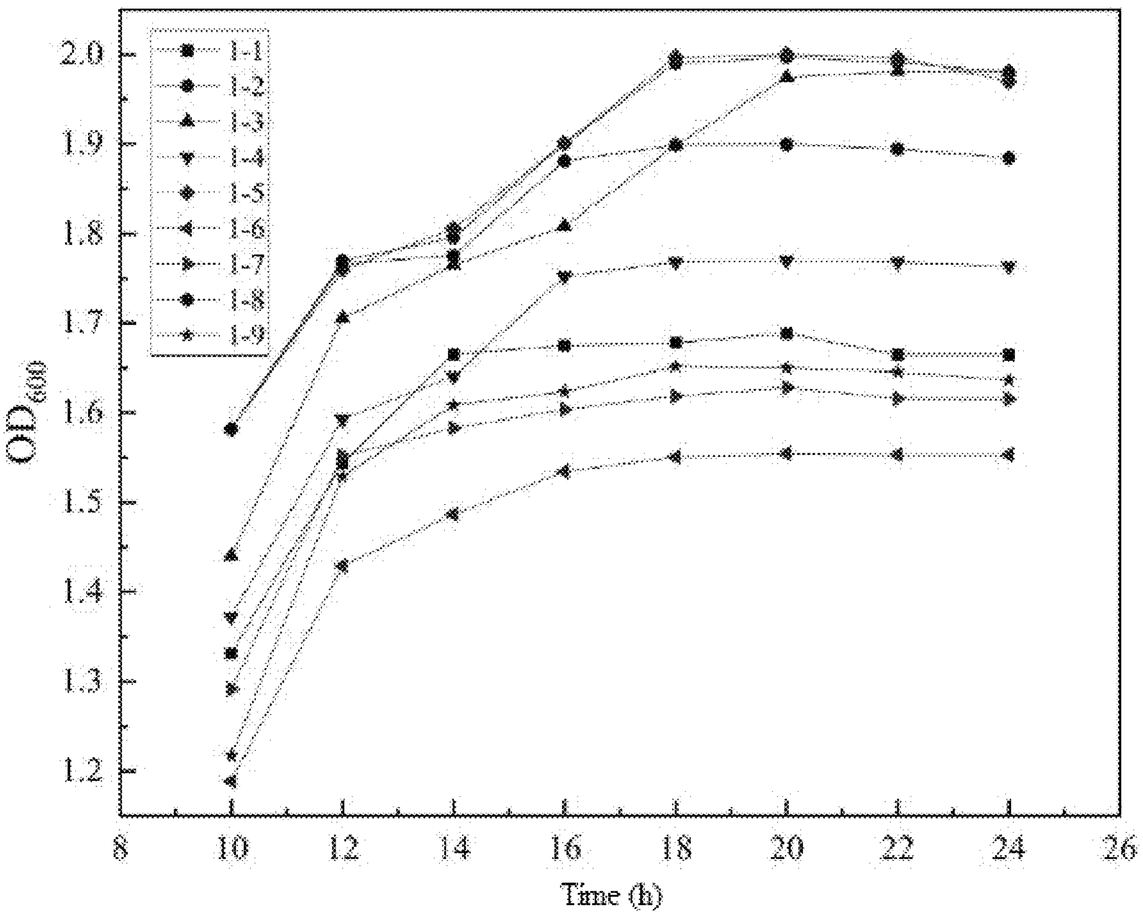
FIG. 4 is a growth curve chart of *Saccharomyces cerevisiae* 1-1, 1-2, 1-3, 1-4, 1-5, 1-6, 1-7, 1-8 and 1-9 in the stable growth period (14-20 h)

Drawing the growth curves for the above 15 strains of *Saccharomyces cerevisiae*, as shown in FIG. 2, which shows that the growth trends of the 15 strains of *Saccharomyces cerevisiae* are basically the same. That is, 0-6 h after culture is a growth lag period of the strain; the number of cells increases geometrically from 6 h to 12 h, and the strains enter a logarithmic growth period; and after the culture time of the strain reaches 14-20 h, the yield of bacteria reaches a highest point, and this period is the stable growth period of the strain. The bacteria in the logarithmic growth period have sufficient nutritional conditions, high growth speed and strong metabolic capacity; and the cell nature in the growth period is relatively stable and uniform and sensitive to changes of physical and chemical factors, and salt stress. Therefore, the cells in the logarithmic growth period are usually selected for experimental research. FIG. 3 and FIG. 4 are detail views of FIG. 2; FIG. 3 is a growth curve chart of *Saccharomyces cerevisiae* Z-1, Z-2, Z-3, Z-4, Z-5, and Z-6 in a stable growth period (14-20 h); it may be seen from the drawing that the growth of *Saccharomyces cerevisiae* Z-1 is better than other strains in the stable growth period, and $OD_{600}$ of *Saccharomyces cerevisiae* Z-1 is more than 2.0; and FIG. 4 is a growth curve chart of *Saccharomyces cerevisiae* 1-1, 1-2, 1-3, 1-4, 1-5, 1-6, 1-7, 1-8 and 1-9 in the stable growth period (14-20 h), and it may be seen by comparison that the growth of *Saccharomyces cerevisiae* 1-2 and 1-5 is better than others in FIG. 4, but $OD_{600}$ of *Saccharomyces cerevisiae* 1-2 and 1-5 is less than 2.0. By comprehensively analyzing *Saccharomyces cerevisiae* Z-1, the growth of *Saccharomyces cerevisiae* Z-1 is better than other 14 strains.

Determining Protein Content:

Inoculating the seed solutions of the 15 strains of *Saccharomyces cerevisiae* numbered in (1) respectively into 300 mL YPD liquid culture medium at an inoculation amount of 1% ($OD_{600}$=0.8), conducting shaking culturing for 48 h at 30° C. and 180 rpm, and obtaining bacterial suspensions. Determining the protein content in each bottle of bacterial suspension, and repeating three times. Screening the strain with the highest protein content.

Centrifuging the bacterial suspension at 4500 rpm for 10 min after 48 h fermentation culture, removing supernatant, washing with distilled water, repeatedly washing three times, drying to constant weight in an oven at 105° C. or freeze drying to constant weight, cooling, and then determining the crude protein content by a protein content determination method specified in GB/T 5009.5-2003 as follows:

$$\text{crude protein (\%)} = \frac{(V_2 - V_1) \times C \times 0.0140 \times 6.25}{m \times V'/V} \times 100$$

In the formula, $V_2$—volume mL of standard hydrochloric acid solution consumed by titration of samples;

$V_1$—volume mL of the standard hydrochloric acid solution required for the blank control;

C—concentration of the standard hydrochloric acid solution;

m—mass g of a test sample;

V—total volume mL of a test sample digestion solution;

V'—volume mL of the digestion solution for distillation;

0.0140—grams of nitrogen per milligram equivalent;

6.25—an average coefficient for converting nitrogen into proteins.

Figure 5:
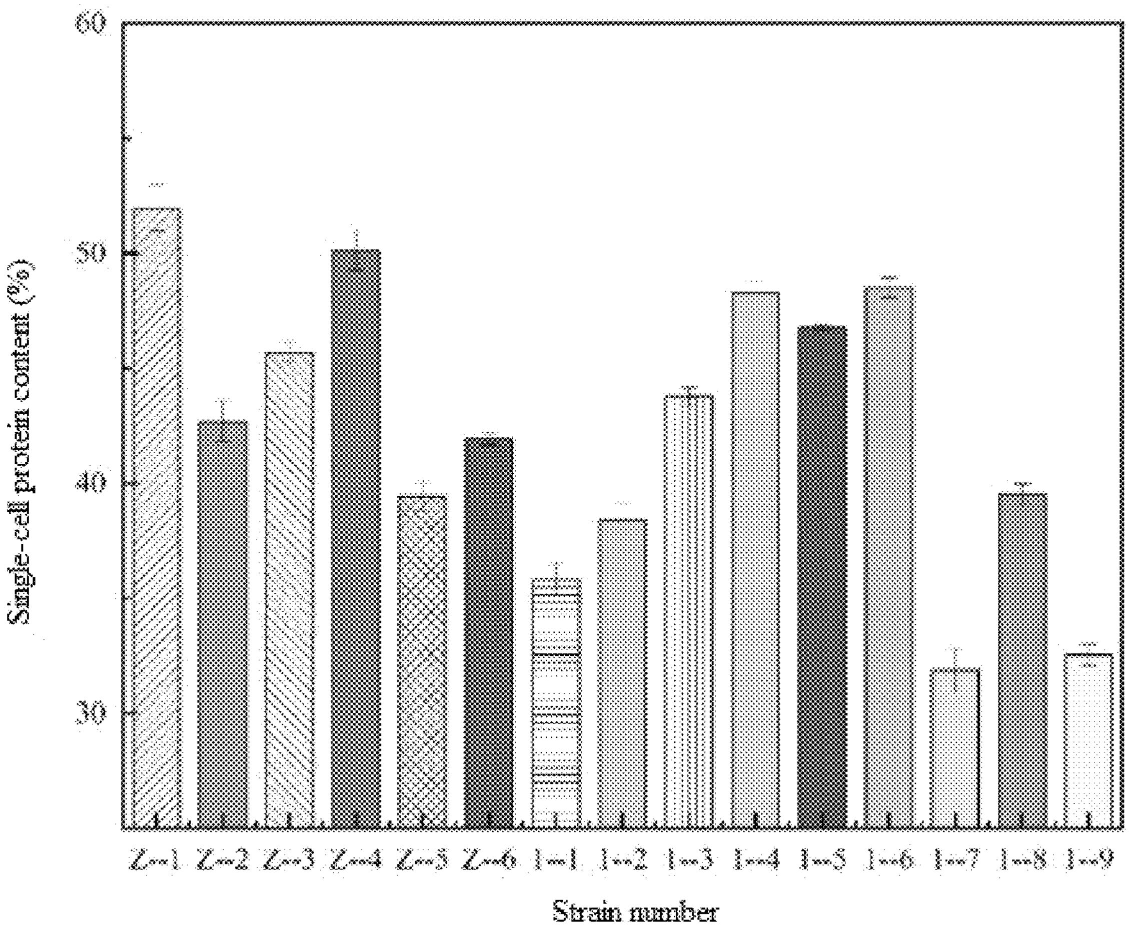
FIG. 5 is a bar diagram of protein content detection results in the present invention.

Detecting the protein content of the above 25 strains of *Saccharomyces cerevisiae*, wherein detection results are shown in the following table, and converted into a more intuitive bar diagram, as shown in FIG. 5.

| Strain number | Single-cell protein content |
|---|---|
| Z-1 | 51.97 ± 0.981Aa |
| Z-2 | 42.7 ± 0.898Efef |
| Z-3 | 45.7 ± 0.432Dd |
| Z-4 | 50.13 ± 0.896Bb |
| Z-5 | 39.43 ± 0.665Gg |
| Z-6 | 41.93 ± 0.287Ff |
| 1-1 | 35.83 ± 0.694Hh |
| 1-2 | 38.4 ± 0.748Gg |
| 1-3 | 43.77 ± 0.403Ee |
| 1-4 | 48.3 ± 0.506Cc |
| 1-5 | 46.77 ± 0.125CDd |
| 1-6 | 48.5 ± 0.432BCc |
| 1-7 | 31.87 ± 0.943Ii |
| 1-8 | 39.53 ± 0.449Gg |
| 1-9 | 32.53 ± 0.478Ii |

Note: different lowercase letters indicate significant difference (P<0.05), and different uppercase letters indicate extremely significant difference (P<0.01).

It may be seen from the above table and FIG. 5 that the single-cell protein content of the 15 strains of *Saccharomyces cerevisiae* is 30%-55%, and the protein content of *Saccharomyces cerevisiae* Z-1, Z-2, Z-3, Z-4, Z-6, 1-3, 1-4 and 1-5 is all more than 40%. The protein content of *Saccharomyces cerevisiae* Z-1 is 51.97%, the protein content of *Saccharomyces cerevisiae* Z-2 is 42.7%, the protein content of *Saccharomyces cerevisiae* Z-3 is 45.7%, the protein content of *Saccharomyces cerevisiae* Z-4 is 50.13%, the protein content of *Saccharomyces cerevisiae* Z-6 is 41.93%, the protein content of *Saccharomyces cerevisiae* 1-3 is 43.77%, the protein content of *Saccharomyces cerevisiae* 1-4 is 48.3%, and the protein content of *Saccharomyces cerevisiae* 1-5 is 46.77%. The single-cell protein content of *Saccharomyces cerevisiae* Z-1 and *Saccharomyces cerevisiae* Z-4 is higher than other strains of *Saccharomyces cerevisiae* and reaches 51.97% and 50.13% respectively. Therefore, *Saccharomyces cerevisiae* Z-1 and *Saccharomyces cerevisiae* Z-4 are screened according to the protein content.

According to results of *Saccharomyces cerevisiae* salt-tolerant screening, growth curve determination and protein content determination, *Saccharomyces cerevisiae* Z-1 is finally determined to be a salt-tolerant strain, and was preserved in Guangdong Microbial Culture Collection Center (GDMCC) on Mar. 3, 2023, with a preservation number of GDMCC NO: 63227 and the preservation address of Floor 5, Building 59, No. 100 Courtyard, Xianlie Middle Road, Guangzhou.

The following tests were conducted on the above *Saccharomyces cerevisiae* Z-1 respectively:

(1) Determining the Growth of *Saccharomyces cerevisiae* Z-1 Under Different Salt Concentration Plates:

Performing gradient dilution for the seed solution ($OD_{600}$=0.8) of *Saccharomyces cerevisiae* Z-1 according to $10^0$, $10^{-1}$, $10^{-2}$, $10^{-3}$ and $10^{-4}$, and collecting 4 μL of each diluted solution, orderly spotting the solution on ammonium sulfate agar culture medium containing 0 mol/L, 0.2 mol/L, 0.4 mol/L, 0.6 mol/L, 0.8 mol/L and 1.0 mol/L $NH_4^+$ respectively, invertedly culturing at 30° C. for 48 h in a thermostatic incubator, and judging the salt tolerance of the strain by observing the size and density of colonies on the culture medium.

Figure 6:
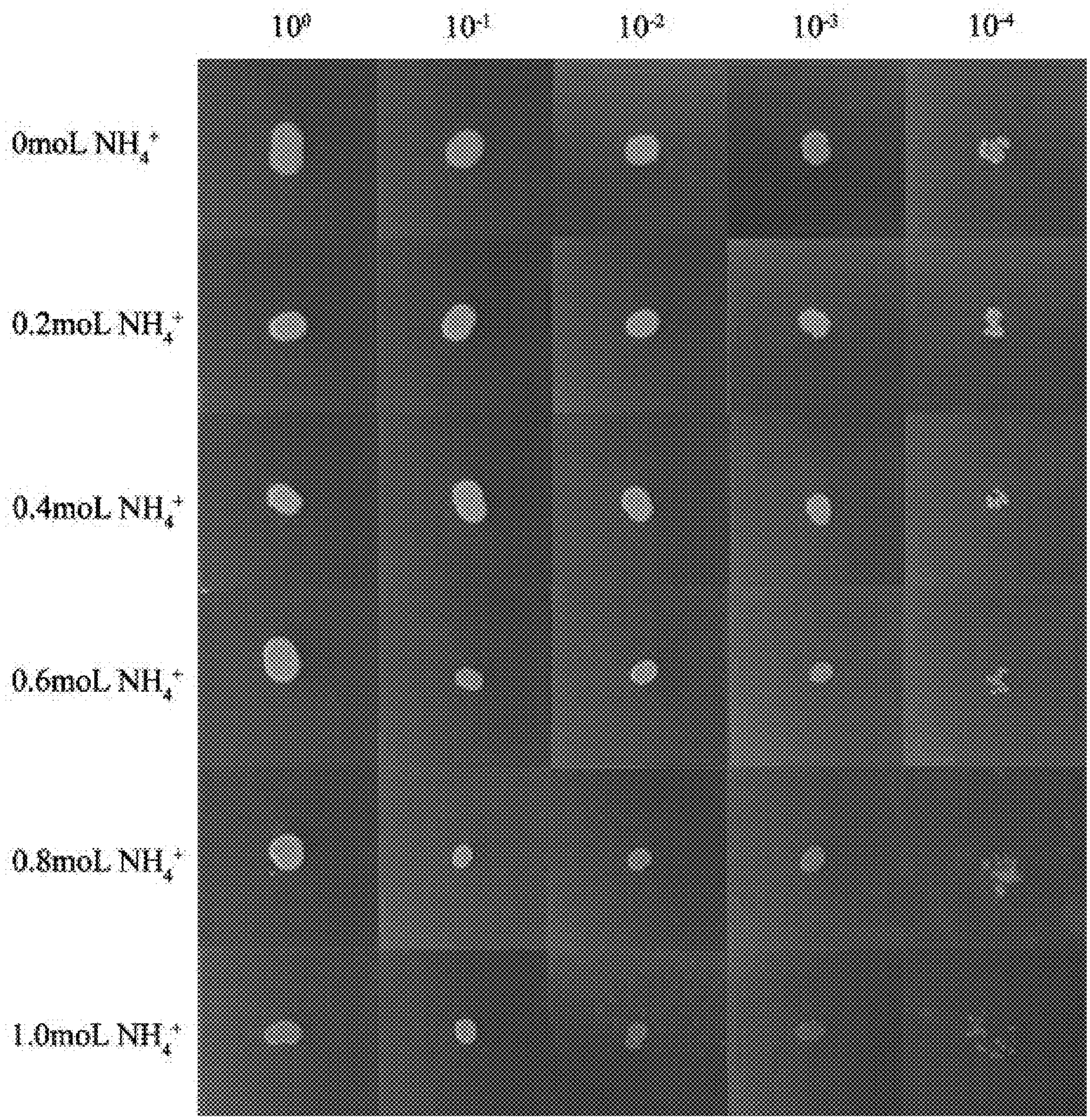
FIG. 6 shows growth situation of *Saccharomyces cerevisiae* Z-1 under different salt concentration plates in the present invention.

The growth of *Saccharomyces cerevisiae* Z-1 under different salt concentration plates is shown in FIG. 6, and it may be seen that there is no obvious difference in the growth of *Saccharomyces cerevisiae* Z-1 without adding $NH_4^+$, and the clear colony growth can be observed at a dilution ratio of $10^{-4}$ after 48 h culture. When the concentration of $NH_4^+$ in the culture medium reaches 0.2 mol/L, there is no great difference between the colony size of *Saccharomyces cerevisiae* Z-1 at a dilution ratio of $10^0$-$10^{-2}$ and the control group (the concentration of $NH_4^+$ is 0 mol/L), and the range of the formed colonies is reduced. The colonies formed by *Saccharomyces cerevisiae* Z-1 at the dilution ratio of $10^{-3}$, $10^{-4}$ are larger and fuller compared with the control group (the concentration of $NH_4^+$ is 0 mol/L). When the concentration of $NH_4^+$ in the culture medium reaches 0.4 mol/L, the clear colony growth of *Saccharomyces cerevisiae* Z-1 at the dilution ratio of $10^0$-$10^{-4}$ can be observed. When the concentration of $NH_4^+$ in the culture medium reaches 0.6 mol/L, *Saccharomyces cerevisiae* Z-1 at the dilution ratio of $10^{-4}$ is slightly inhibited. When the concentration of $NH_4^+$ in the culture medium reaches 0.8 mol/L, *Saccharomyces cerevisiae* Z-1 at the dilution ratio of $10^{-4}$ is slightly inhibited, and the colony becomes smaller. When the concentration of $NH_4^+$ in the culture medium reaches 1.0 mol/L, *Saccharomyces cerevisiae* Z-1 at a dilution ratio of $10^{-4}$ is inhibited, the range of colonies is reduced, and *Saccharomyces cerevisiae* Z-1 can grow in a concentration of 1.0 mol/L $NH_4^+$.

(2) Determining the Growth Curve of *Saccharomyces cerevisiae* Z-1 at Different Salt Concentrations:

Inoculating the seed solution of *Saccharomyces cerevisiae* Z-1 respectively into YPD liquid culture medium containing 0 mol/L, 0.2 mol/L, 0.4 mol/L, 0.6 mol/L, 0.8 mol/L and 1.0 mol/L $NH_4^+$ at an inoculation amount of 1% ($OD_{600}$=0.8), and at the same time preparing a group of blank control (the culture medium is not inoculated with *Saccharomyces cerevisiae* Z-1). Conducting shaking culturing for 48 h at 30° C. and 180 rpm, sampling once every 4 h, collecting 3 mL of sample each time, setting zero for the blank control, determining a light absorption value of *Saccharomyces cerevisiae* at 600 nm, and then drawing the growth curve with the light absorption value of *Saccharomyces cerevisiae* Z-1 as a vertical axis and growth time as a horizontal axis.

Figure 7:
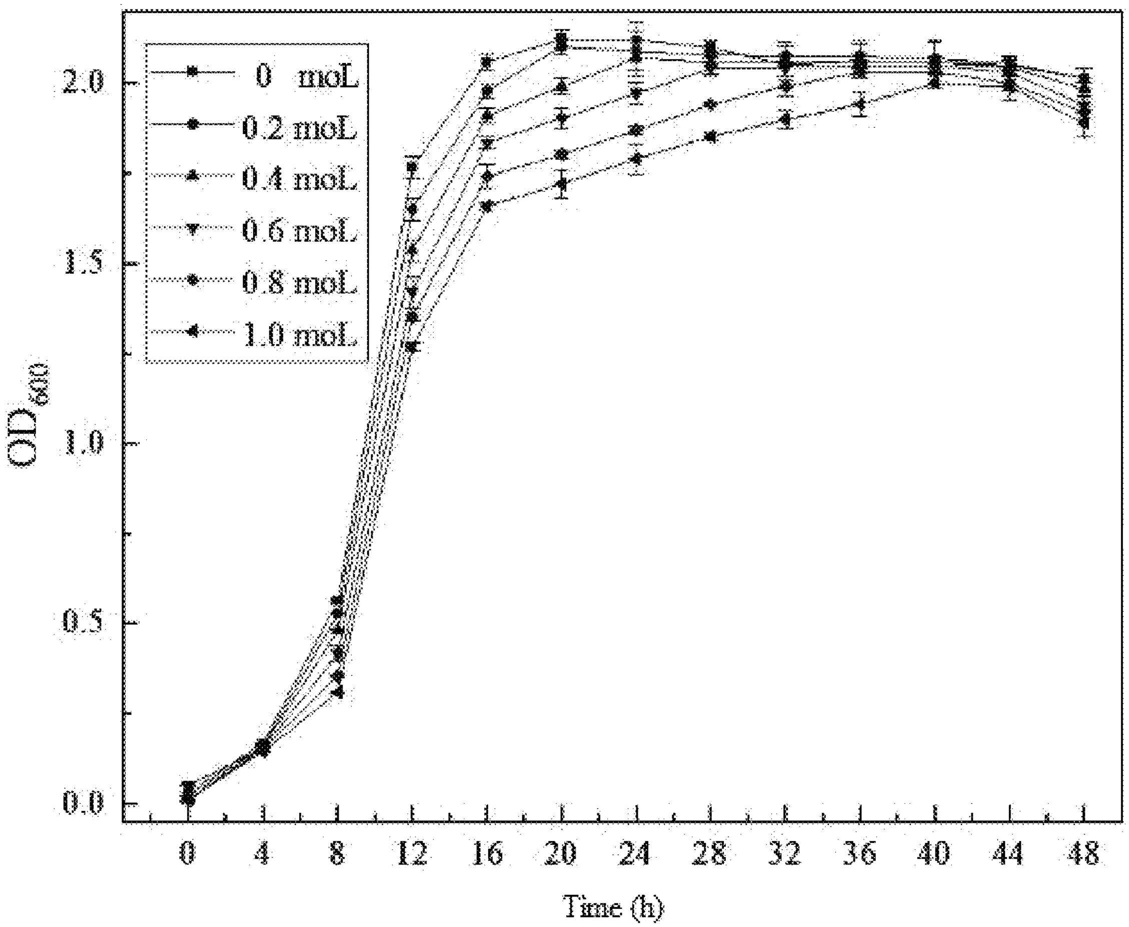
FIG. 7 shows growth curve determination results of *Saccharomyces cerevisiae* Z-1 under different salt concentrations in the present invention.

The drawn growth curve is as shown in FIG. 7. It may be seen from the drawing that when the concentration of $NH_4^+$ reaches 0.2 mol/L, there is no significant difference in the growth capacity of *Saccharomyces cerevisiae* Z-1 compared with the control group. When the concentration of $NH_4^+$ reaches 0.4 mol/L, the growth capacity of *Saccharomyces cerevisiae* Z-1 decreases. When the concentration of $NH_4^+$ reaches 0.6 mol/L, the growth capacity of *Saccharomyces cerevisiae* Z-1 decreases, and there is a certain lag period. When the concentration of $NH_4^+$ reaches 0.8 mol/L, the growth capacity of *Saccharomyces cerevisiae* Z-1 decreases obviously. When the concentration of $NH_4^+$ reaches 1.0 mol/L, the growth capacity of *Saccharomyces cerevisiae* Z-1 decreases particularly obviously, and *Saccharomyces cerevisiae* Z-1 grows slowly and reaches the stable period after 16 h.

The ammonium sulfate-tolerant *Saccharomyces cerevisiae* Z-1 provided by the present invention may grow and breed in an environment containing 1.0 mol/L $NH_4^+$ (6.6% ammonium sulfate), and not only can adapt to a hyperosmotic environment of solid-state fermentation, but also can be transformed into proteins by using the relatively cheap ammonium sulfate inorganic salt; compared with the existing strains, the protein content of the strain of the present invention can reach 51.97%; and as a fermentation strain for the protein feed, the strain of the present invention not only can adapt to the high-tolerance environment, but also can increase the protein content of the protein feed, and is an excellent strain for solid-state fermentation.

The above embodiment is merely one of preferred embodiments of the present invention, and shall not be used to limit the protection scope of the present invention. However, any meaningless changes or embellishments made within the main design concept and spirit of the present invention, which still solves the technical problems consistent with the present invention, shall fall within the protection scope of the present invention.

What is claimed is:

1. A screening method of the ammonium sulfate-tolerant *Saccharomyces cerevisiae*, comprising the following steps:

S1: separating a plurality of strains of *Saccharomyces cerevisiae* from fermentation broth of grapes, obtaining seed solutions, and numbering the seed solutions of the plurality of strains of *Saccharomyces cerevisiae;*

S2: preliminarily screening salt-tolerant *Saccharomyces cerevisiae*: inoculating the seed solutions of *Saccharomyces cerevisiae* numbered in S1 into ammonium sulfate agar culture media with different concentrations of $NH_4^+$ respectively for culture to obtain cultured strains of *Saccharomyces cerevisiae*, and screening according to bacterial colony diameters of the cultured strains of *Saccharomyces cerevisiae* to obtain 3-5 strains of *Saccharomyces cerevisiae* with largest bacterial colony diameters;

S3: determining growth curves: inoculating the seed solutions of *Saccharomyces cerevisiae* numbered in S1 into YPD liquid culture medium respectively for culture, drawing growth curves, determining a stable growth period which is a period from 14 to 20 hours of culture time, and screening 3-5 strains of *Saccharomyces cerevisiae* with $OD_{600}$ of more than 2.0 during the stable growth period;

S4: determining protein content: inoculating the seed solutions of *Saccharomyces cerevisiae* numbered in S1 into the YPD liquid culture medium for culture to obtain bacterial suspensions, measuring protein contents in the bacterial suspensions after the culture, and screening according to the measured protein contents to obtain 3-5 strains of *Saccharomyces cerevisiae* with highest protein contents;

S5: comprehensively analyzing and comparing *Saccharomyces cerevisiae* screened in S2, S3 and S4 to select the strain of *Saccharomyces cerevisiae* with the largest bacterial colony diameter, the $OD_{600}$ of more than 2.0 and the highest protein content.

2. The screening method of the ammonium sulfate-tolerant *Saccharomyces cerevisiae* according to claim 1, wherein 15 strains of *Saccharomyces cerevisiae* are separated from the fermentation broth of grapes in step S1 and numbered respectively as: Z-1, Z-2, Z-3, Z-4, Z-5, Z-6, 1-1, 1-2, 1-3, 1-4, 1-5, 1-6, 1-7, 1-8 and 1-9.

3. The screening method of the ammonium sulfate-tolerant *Saccharomyces cerevisiae* according to claim 2, wherein specific operation steps of determining the growth curves in step S2 are as follows: collecting 4 μL of the seed solutions of the 15 separated strains of *Saccharomyces cerevisiae*, orderly spotting the seed solutions on ammonium sulfate agar culture media containing 0 mol/L, 0.2 mol/L, 0.4 mol/L, 0.6 mol/L, 0.8 mol/L, 1.0 mol/L, and 1.2 mol/L $NH_4^+$, and invertedly culturing for 48 h at 30° C. in a thermostatic incubator; and repeating 3 times for each level, and screening according to bacterial colony diameters of strains of *Saccharomyces cerevisiae* obtained after 48 h culture to obtain the 3-5 strains of *Saccharomyces cerevisiae* with largest bacterial colony diameters.

4. The screening method of the ammonium sulfate-tolerant *Saccharomyces cerevisiae* according to claim 2, wherein a specific method of determining the growth curves in step S3 is as follows: inoculating the seed solutions of the 15 strains of *Saccharomyces cerevisiae* separated in step S1 respectively into 300 mL YPD liquid culture medium at an inoculation amount of 1%, preparing a group of blank control without inoculating the seed solution of *Saccharomyces cerevisiae* at the same time, conducting shaking culturing at 30° C. and 180 rpm, collecting 3 mL of sample respectively at 0 h, 2 h, 4 h, 6 h, 8 h, 10 h, 12 h, 14 h, 16 h, 18 h, 20 h, 22 h and 24 h after inoculation, setting zero for the blank control, determining a light absorption value of *Saccharomyces cerevisiae* at 600 nm, then drawing the growth curve with the light absorption value of *Saccharomyces cerevisiae* as a vertical axis and growth time as a horizontal axis, and screening 3-5 strains of *Saccharomyces cerevisiae* with $OD_{600}$ of more than 2.0 during the stable growth period.

5. The screening method of the ammonium sulfate-tolerant *Saccharomyces cerevisiae* according to claim 2, wherein a specific method of determining the protein content in step S4 is as follows: inoculating the seed solutions of the 15 strains of *Saccharomyces cerevisiae* separated in the step S1 respectively into 300 mL YPD liquid culture medium at the inoculation amount of 1%, and conducting shaking culturing for 48 h at 30° C. and 180 rpm to obtain the bacterial suspensions; determining the protein content in each bottle of bacterial suspension; and screening 3-5 strains of *Saccharomyces cerevisiae* with high protein content.

6. The screening method of the ammonium sulfate-tolerant *Saccharomyces cerevisiae* according to claim 1, wherein $OD_{600}$ of the seed solutions of *Saccharomyces cerevisiae* in the steps S2, S3 and S4 is the same.

7. The screening method of the ammonium sulfate-tolerant *Saccharomyces cerevisiae* according to claim 4, wherein when the protein content in each bottle of bacterial suspension is determined in the step S4, each group is repeated three times, and a specific operation method is as follows:

centrifuging the bacterial suspension at 4500 rpm for 10 min after 48 h fermentation culture, removing supernatant, washing with distilled water, repeatedly washing three times, drying to constant weight in an oven at 105° C. or freeze drying to constant weight, cooling, and then determining the crude protein content by a Kjeldahl method as follows:

$$\text{crude protein }(\%) = \frac{(V_2 - V_1)\times C\times 0.0140\times 6.25}{m\times V'/V}\times 100$$

in the formula, $V_2$—volume mL of standard hydrochloric acid solution consumed by titration of samples;

$V_1$—volume mL of the standard hydrochloric acid solution required for the blank control;

C—concentration of the standard hydrochloric acid solution;

m—mass g of a test sample;

V—total volume mL of a test sample digestion solution;

V'—volume mL of the digestion solution for distillation;

0.0140—grams of nitrogen per milligram equivalent;

6.25—an average coefficient for converting nitrogen into proteins.

* * * * *